United States Patent
Sashida (10) Patent No.: US 11,449,991 B2
(45) Date of Patent: Sep. 20, 2022

(54) IMAGE PROCESSING METHOD, IMAGE PROCESSING APPARATUS, AND STORAGE MEDIUM

(71) Applicant: Konica Minolta, Inc., Tokyo (JP)

(72) Inventor: Takehiko Sashida, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 59 days.

(21) Appl. No.: 16/977,202

(22) PCT Filed: Feb. 15, 2019

(86) PCT No.: PCT/JP2019/005571
§ 371 (c)(1),
(2) Date: Sep. 1, 2020

(87) PCT Pub. No.: WO2019/171909
PCT Pub. Date: Sep. 12, 2019

(65) Prior Publication Data
US 2021/0012491 A1  Jan. 14, 2021

(30) Foreign Application Priority Data

Mar. 8, 2018  (JP) .............................. JP2018-041377

(51) Int. Cl.
*G06T 7/00* (2017.01)
*G06T 7/90* (2017.01)
(Continued)

(52) U.S. Cl.
CPC .............. *G06T 7/0012* (2013.01); *G06T 7/90* (2017.01); *G06V 10/56* (2022.01); *G06V 10/60* (2022.01);
(Continued)

(58) Field of Classification Search
CPC ..................... G06T 7/0012; G06T 7/90; G06T 2207/10024; G06T 2207/10116;
(Continued)

(56) References Cited

U.S. PATENT DOCUMENTS

2005/0226486 A1* 10/2005 Tsujii ..................... G16H 50/30
382/132
2013/0301900 A1* 11/2013 Kiyuna ................... G06T 11/60
382/133

(Continued)

FOREIGN PATENT DOCUMENTS

JP  2013238459  11/2013
JP  5533662     6/2014
(Continued)

OTHER PUBLICATIONS

Yamaguchi, "Color Information Processing of Image for Digital Pathology," Pathology & Clinical Medicine, vol. 35(1), pp. 41-47 (2017).

(Continued)

*Primary Examiner* — Ali Bayat
(74) *Attorney, Agent, or Firm* — BakerHostetler (57) ABSTRACT

An image processing method includes image inputting, auxiliary information inputting, image processing, feature quantity extracting, and discriminating. The image inputting is inputting a cell image. The auxiliary information inputting is inputting auxiliary information on a color of the cell image. The image processing is generating multiple processed images by performing a different image-processing process on the cell image based on the auxiliary information. The feature quantity extracting is extracting a feature quantity of a discrimination target from each of the multiple (Continued)

processed images. The discriminating is discriminating the discrimination target in the cell image based on the feature quantity.

9 Claims, 8 Drawing Sheets

(51) Int. Cl.
*G06V 10/56* (2022.01)
*G06V 10/60* (2022.01)

(52) U.S. Cl.
CPC ............... *G06T 2207/10024* (2013.01); *G06T 2207/10116* (2013.01); *G06T 2207/30024* (2013.01)

(58) Field of Classification Search
CPC ........... G06T 2207/30024; G06T 2207/10056; G06K 9/4652; G06K 9/4661; G01N 33/48; G01N 33/483
USPC ......................................................... 382/128
See application file for complete search history.

(56) References Cited

U.S. PATENT DOCUMENTS

| 2017/0193655 | A1* | 7/2017 | Madabhushi | ......... G06T 7/0012 |
| 2017/0193657 | A1* | 7/2017 | Madabhushi | ........ G06K 9/3233 |

FOREIGN PATENT DOCUMENTS

| WO | 2016136441 | 9/2016 |
| WO | 2018128091 | 7/2018 |
| WO | 2018131091 | 7/2018 |

OTHER PUBLICATIONS

International Search Report issued in PCT/JP2019/005571, dated May 21, 2019.
International Preliminary Report on Patentability issued in PCT/JP2019/005571, dated Sep. 8, 2020.
Japan Patent Application No. 2020-504890; Notice of Reasons for Refusal; dated May 10, 2022; 6 pages.

* cited by examiner

BRIGHT  —1  0  1  DARK
LUMINOSITY DISTRIBUTION

BRIGHT  —1  0  1  DARK

FIG.5B

LUMINOSITY DISTRIBUTION

IMAGE PROCESSING METHOD, IMAGE PROCESSING APPARATUS, AND STORAGE MEDIUM

The present U.S. Patent Application is U.S. National Phase Application under 35 U.S.C. 371 of International Application PCT/JP2019/005571 filed on Feb. 15, 2019, which claims a priority to JP Application No. 2018-041377 filed on Mar. 8, 2018, the entire disclosures of which are incorporated herein by reference in their entireties.

TECHNICAL FIELD

The present disclosure relates to an image processing method, an image processing apparatus, and a program, and more particularly to image processing performed for pathological diagnosis.

BACKGROUND

Methods for automatically discriminating observation target regions in images with the image recognition technologies have been widely used. In image recognition technologies, it is typical to extract useful feature quantities from an image for discriminating the observation target and then perform processing with a discrimination circuit based on machine learning.

For example, patent literature 1 discloses a method for processing X-ray images with an image recognition technology. Parameters appropriate for processing X-ray images depend on imaged parts and imaging directions of the X-ray imaging. According to the method, a discrimination circuit constructed by machine learning judges the imaged part and the imaging direction of an X-ray image. On the basis of the judged imaged part and imaging direction, an image process is selected.

Methods for automatically discriminating cell regions in a cell image with image recognition technologies have also been widely investigated for pathological diagnosis. In pathological diagnosis, discriminating types of cells and estimating the forms of cells on the basis of microscope images of the cells are vital processes to judge the type and state of a disease appearing at internal organs. Such processes necessitate judgements by specialists, such as pathologists. With image recognition technologies, however, cells can be automatically discriminated without human work. This largely reduces burdens on medical sites.

CITATION LIST

Patent Literature

[Patent Literature 1] JP5533662

SUMMARY OF INVENTION

Technical Problem

Constructing useful feature quantities is crucial for discriminating cells with image recognition technologies. Conventionally, feature quantities for machine learning have been constructed by humans to be suitable for discrimination targets. In recent years, deep learning has been actively utilized to perform automatic construction of feature quantities and cell discrimination with the feature quantities together.

In extracting feature quantities with a typical image recognition technology, feature quantities are sufficiently extracted from one input image. However, a pathologist often discriminates cells on the basis of preliminary knowledge on the discrimination target, the patient, the imaged region, and so forth, as well as an image. To appropriately discriminate cells, features extracted from only one image are insufficient. For example, in discriminating a type of cell on the basis of shades of colors, the following (i) and (ii) have largely different meanings: (i) difference in shades between the type of cell and the surroundings and (ii) difference in shades between the type of cell and the standard staining density of the type of cell. Features of these differences are difficult to judge on the basis of one image.

The present invention has been made in views of the above issues. Objects of the present invention include providing an image processing method, an image processing apparatus, and a program that can discriminate cells accurately in discriminating cells with image recognition technologies.

Solution to Problem

In order to solve the abovementioned problems, an image processing method described in claim 1 includes:

image inputting that is inputting a cell image;

auxiliary information inputting that is inputting auxiliary information on a color of the cell image;

image processing that is generating multiple processed images by performing a different image-processing process on the cell image based on the auxiliary information;

feature quantity extracting that is extracting a feature quantity of a discrimination target from each of the multiple processed images; and discriminating that is discriminating the discrimination target in the cell image based on the feature quantity.

The invention described in claim 2 is the image processing method according to claim 1, wherein the auxiliary information is information on a color of each of a specific region in the cell image, and the image processing is generating the multiple processed images by performing the image-processing process for each of the specific region.

The invention described in claim 3 is the image processing method according to claim 2, wherein the image processing is generating the multiple processed images by performing, as the image-processing process, a normalization process that uses a luminosity average and a luminosity variance of each of the region to which a cell belongs.

The invention described in claim 4 is the image processing method according to any one of claims 1 to 3, wherein the auxiliary information is information on a color of each of a type of cell, and the image processing is generating the multiple processed images by performing the image-processing process for each of the type of cell.

The invention described in claim 5 is the image processing method according to claim 4, wherein the image processing is generating the multiple processed images by performing, as the image-processing process, a normalization process that uses a luminosity average and a luminosity variance of each of the type of cell.

The invention described in claim 6 is the image processing method according to any one of claims 1 to 5, wherein the auxiliary information is information on a color of the cell image under each of a staining condition, and the image processing is generating the multiple processed images by performing the image-processing process based on the staining condition of the cell image.

The invention described in claim 7 is the image processing method according to claim 6, wherein the image processing is generating the multiple processed images by performing, as the image-processing process, a normalization process that uses a luminosity average and a luminosity variance of each of the staining condition.

The invention described in claim 8 is the image processing method according to any one of claims 1 to 7, wherein the feature quantity extracting and the discriminating are performed together.

The invention described in claim 9 is an image processing apparatus, including:

an image inputter that inputs a cell image;

an auxiliary information inputter that inputs auxiliary information on a color of the cell image;

an image processor that generates multiple processed images by performing a different image-processing process on the cell image based on the auxiliary information;

a feature quantity extractor that extracts a feature quantity of a discrimination target from each of the multiple processed images; and a discriminator that discriminates the discrimination target in the cell image based on the feature quantity.

A program described in claim 10 causes a computer of an image forming apparatus including an image inputter that inputs a cell image and an auxiliary information inputter that inputs auxiliary information on a color of the cell image to function as:

an image processor that generates multiple processed images by performing a different image-processing process on the cell image based on the auxiliary information;

a feature quantity extractor that extracts a feature quantity of a discrimination target from each of the multiple processed images; and a discriminator that discriminates the discrimination target in the cell image based on the feature quantity.

Advantageous Effects of Invention

The present invention can provide an image processing method, an image processing apparatus, and a program that can discriminate cells accurately with image recognition technologies.

DESCRIPTION OF EMBODIMENTS

Hereinafter, preferred embodiments of the present invention are described with reference to the drawings. The embodiments are not intended to limit the present invention.

<Configuration of Pathological Diagnosis Support System 10>

Figure 1:
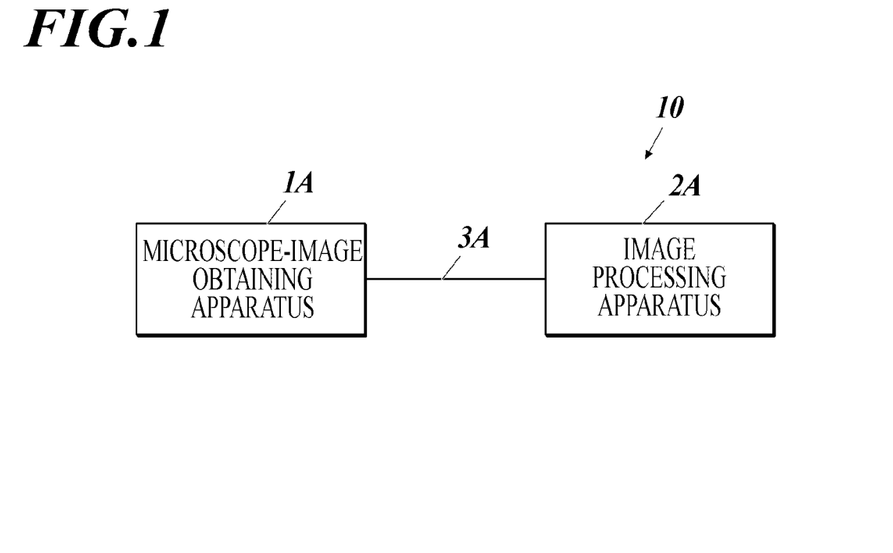
FIG. 1 is a system configuration of a pathological diagnosis support system to which a biological substance quantitation method of this invention is applied.

FIG. 1 exemplifies an overall configuration of a pathological diagnosis support system 10.

The pathological diagnosis support system 10 obtains a microscope image of a tissue section of a human body stained with specific staining reagents, analyzes the obtained microscope image, and discriminates types of cells in the image (hereinafter called cell discrimination).

As shown in FIG. 1, the pathological diagnosis support system 10 includes a microscope-image obtaining apparatus 1A and an image processing apparatus 2A. The apparatuses 1A and 2A are connected to each other for data exchange via an interface, such as a cable 3A.

The method of connecting the microscope-image obtaining apparatus 1A and the image processing apparatus 2A is not limited to a particular method. For example, the microscope-image obtaining apparatus 1A and the image processing apparatus 2A may be connected via a Local Area Network (LAN) cable or may be connected wirelessly.

The microscope-image obtaining apparatus 1A is a well-known microscope having a camera. The microscope-image obtaining apparatus 1A obtains a microscope image of a tissue section on a slide placed on a slide fixing stage and sends the image to the image processing apparatus 2A. The microscope-image obtaining apparatus 1A includes an irradiating unit, an image forming unit, an imaging unit, and a communication interface (I/F). The irradiating unit includes a light source and a filter. The irradiating unit irradiates, with light, the tissue section on the slide placed on the slide fixing stage. The image forming unit includes an ocular lens and an object lens. The image forming unit forms an image with transmitted light and/or reflected light from the tissue section irradiated with light on the slide. The imaging unit is a microscope-mounted camera that includes a charge coupled device (CCD) sensor. The imaging unit captures an image formed on an image forming face by the image forming unit and generates digital image data of the microscope image. The communication I/F sends the generated image data of the microscope image to the image processing apparatus 2A.

The microscope-image obtaining apparatus 1A includes a bright field unit into which the irradiating unit and the image forming unit are combined to be suitable for bright field observation.

The microscope-image obtaining apparatus 1A may not be a microscope having a camera. The microscope-image obtaining apparatus 1A may be an apparatus for creating a virtual microscope slide that obtains a microscope image of the entire tissue section by scanning the slide on the slide fixing stage of the microscope (for example, see JP2002-514319A). The apparatus for creating a virtual microscope slide can obtain image data such that the entire tissue section on the slide is viewable at one time on a display.

The image processing apparatus 2A analyzes the microscope image sent from the microscope-image obtaining apparatus 1A, performs cell discrimination for the cell image, and displays classification of the cells such that a user can visually recognize the classification.

Figure 2:
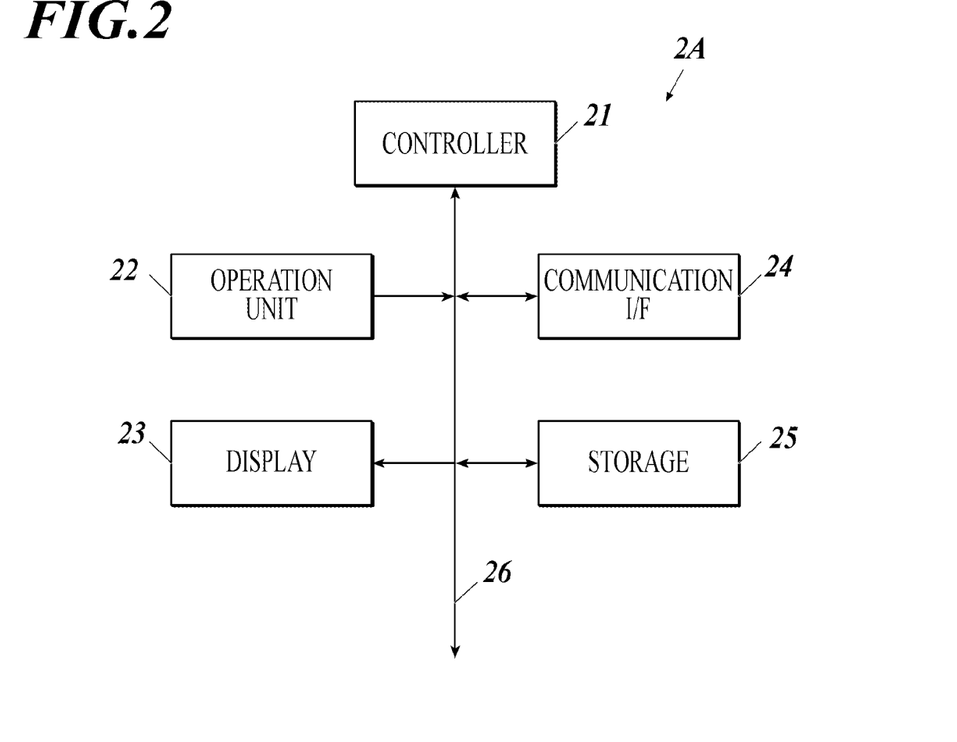
FIG. 2 is a block diagram showing functional components of an image processing apparatus in FIG. 1.

FIG. 2 exemplifies functional components of the image processing apparatus 2A.

As shown in FIG. 2, the image processing apparatus 2A includes a controller 21, an operation unit 22, a display 23, a communication I/F 24, and a storage 25. These components are connected to each other through a bus 26.

The controller 21 includes a central processing unit (CPU) and a random access memory (RAM). The controller 21 performs various processes in cooperation with various programs stored in the storage 25 and integrally controls operation of the image processing apparatus 2A.

For example, the controller 21 performs an image analysis process (see FIG. 6) in cooperation with an image processing program stored in the storage 25, thereby functioning as an image processor, a feature quantity extractor, and a discriminator.

The operation unit 22 includes a keyboard having character entry keys, numeric keys, and various function keys and a pointing device, such as a mouse. The operation unit 22 outputs, to the controller 21, pressing signals of a pressed key on the keyboard and operation signals of the mouse as input signals. The operation unit 22 functions as an auxiliary information inputter for a user inputting auxiliary information.

The display 23 includes a monitor, such as a cathode ray tube (CRT) and a liquid crystal display (LCD). The display 23 displays various screens in accordance with instructions of display signals input by the controller 21.

The communication I/F 24 is an interface for exchanging data with external devices including the microscope-image obtaining apparatus 1A. The communication I/F 24 functions as an image inputter that inputs cell images.

The storage 25 includes a hard disk drive (HDD) and/or a nonvolatile semiconductor memory, for example. The storage 25 stores various programs, various kinds of data, and so forth as described above.

The storage 25 also stores a correct discrimination image(s) that includes information on (i) feature quantities of samples (cells) in the image and (ii) correct classification labels (types of cells) for the respective samples. The storage 25 also stores conditions for extracting feature quantities. The conditions are constructed by the user beforehand. The storage 25 also stores parameters (discrimination conditions) for processes (e.g., color conversion, conversion into a monochrome image) according to types of cells and staining information to generate discrimination images.

The image processing apparatus 2A may also include a LAN adaptor and a router so as to be connected to external devices through a communication network, such as a LAN.

In this embodiment, the image processing apparatus 2A performs analysis using microscope images (cell images) sent from the microscope-image obtaining apparatus 1A.

Cell images are microscope images obtained by the microscope-image obtaining apparatus 1A and showing forms of cells in tissue sections. The microscope-image obtaining apparatus 1A obtains a cell image in a bright field by forming and capturing an enlarged image of a tissue section stained with a staining reagent(s). Staining reagent can stain specific components of a cell, such as a cell nucleus and a cell membrane. Examples of such staining reagents include a hematoxylin staining reagent (H-staining reagent) and a hematoxylin-eosin staining reagent (HE-staining reagent). Hematoxylin (H) is a bluish violet dye that stains, for example, cell nuclei, bony tissue, part of cartilaginous tissue, and serous components (e.g., basophilic tissue).

Eosin (E) is a red to pink dye that stains, for example, cytoplasm, connective tissue of soft tissue, red blood cells, fibrin, and endocrine granules (e.g., acidophilic tissue). A kind of protein in the tissue section may be stained by immunostaining, such as diaminobenzidine (DAB) staining.

<Operation of Pathological Diagnosis Support System 10 (Including Image Processing Method)>

Hereinafter, operation of image processing by the pathological diagnosis support system 10 is described. The image processing includes obtaining the above-described cell image and extracting a region of an observation target. In this embodiment, a microscope image to be used is obtained by imaging a tissue section taken from a human body, as an example.

Initially, an operator stains the tissue section with the HE staining reagent according to a well-known method.

A cell image is then obtained with the microscope-image obtaining apparatus 1A according to the following steps (a1) to (a3).

(a1) The operator places, on a slide, the tissue section in which a nucleus (nuclei) is stained with the HE staining reagent. The operator then places the slide on the slide fixing stage of the microscope-image obtaining apparatus 1A.

(a2) Set the bright field unit, adjust the capturing magnification and focus, and position the observation target region of the tissue section in the visual field.

(a3) Perform imaging with the imaging unit, generate image data of the cell image, and send the image data to the image processing apparatus 2A.

The image processing apparatus 2A then performs image processing on the basis of the cell image. In this embodiment, the image processing apparatus 2A performs normalization processing as the image processing.

The normalization processing is described with reference to FIG. 3. The normalization processing adjusts conditions concerning, for example, luminosity averages and luminosity variances to reduce effects of variations irrelevant to features to be extracted. Such variations, generated during imaging, include difference in tone between different images. The normalization processing allows captured images to be compared under the same condition. This enables stable feature extraction.

Figure 3:
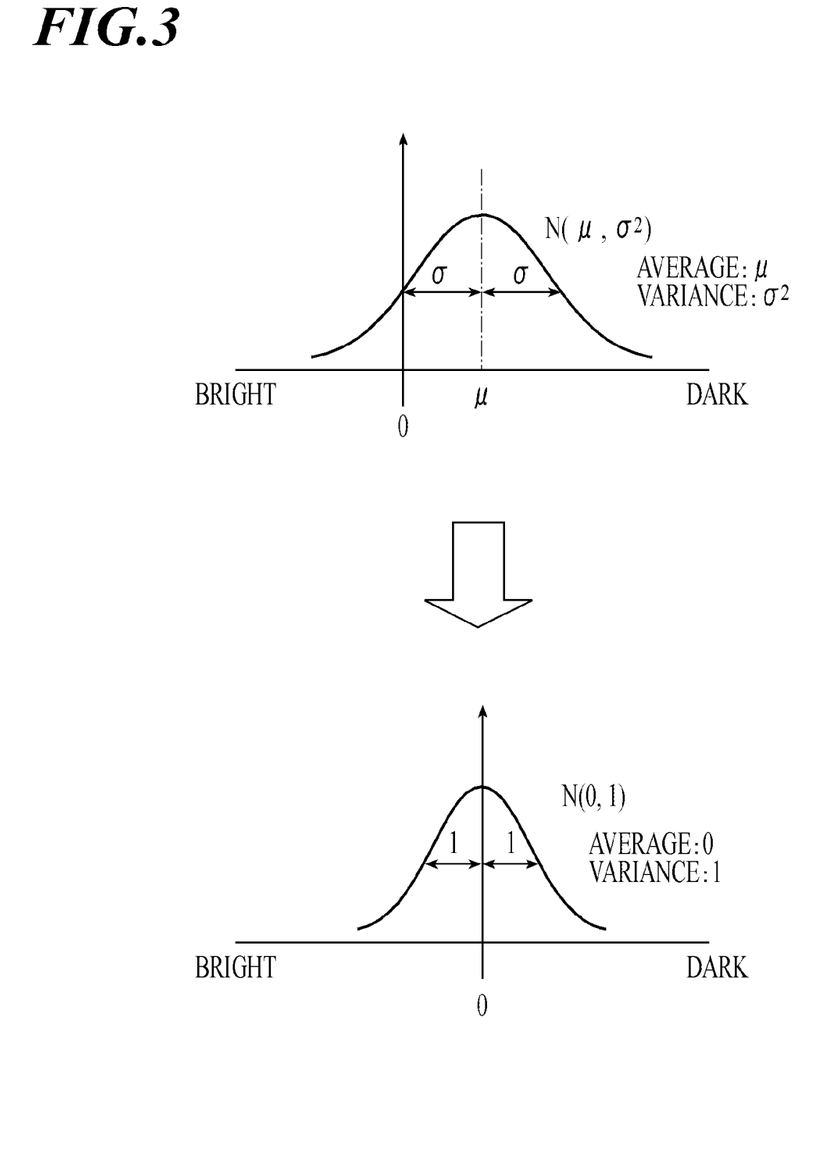
FIG. 3 shows diagrams for explaining a method of typical normalization processing.

As shown in FIG. 3, assume that the luminosity distribution of a cell image follows a normal distribution N ($\mu$, $\sigma^2$), wherein $\mu$ is the luminosity average, and $\sigma^2$ is the luminosity variance. Luminosity averages of respective images are typically adjusted to an identical value, for example, zero. This reduces effects caused by variation in tone of lighting, for example, and makes it easier to recognize deviation (bright or dark) from a reference luminosity as a feature. Further, luminosity variances of respective images are adjusted to an identical value, for example, one. This is as effective as making dynamic ranges uniform, and makes it easier to recognize small variations in luminosity. Thus, the normalization processing makes overall tone, colors, and the like of the images uniform and thereby allows different images to be compared with one another.

However, cell images differ from normal images in that staining is performed. A specialist, such as a pathologist, performs comprehensive cell discrimination in a cell image from various perspectives. For example, the pathologist performs cell discrimination on the basis of (i) tone and colors of the entire cell image, (ii) shades of the entire cell image as compared with a standard color-material density of a region stained under a certain staining condition (hereinafter called standard staining density), and (iii) deviations from the standard staining densities of respective regions in tissue, such as a tumor region, an interstitial region, and a vitreous region.

Therefore, normalizing one cell image under the above-described single condition may not adjust luminosity conditions for every region in the cell image, and may decrease accuracy of feature quantity extraction. In this embodiment, normalization processing is performed on one cell image under multiple conditions to generate multiple processed images.

Hereinafter, respective kinds of normalizing processing according to this embodiment are described.

Normalization processing based on standard staining densities is described with reference to FIG. 4.

For a region stained under a certain staining condition and having a standard staining density, the luminosity average is $\alpha_1$ and the luminosity variance is $\beta_1$. The following formula is applied to a signal $X_1$ of the original image.

$$Z_1=(X_1-\alpha_1)/\sqrt{\beta_1} \qquad (1)$$

Thus, normalization processing based on the standard staining density can be performed.

Figure 4A:
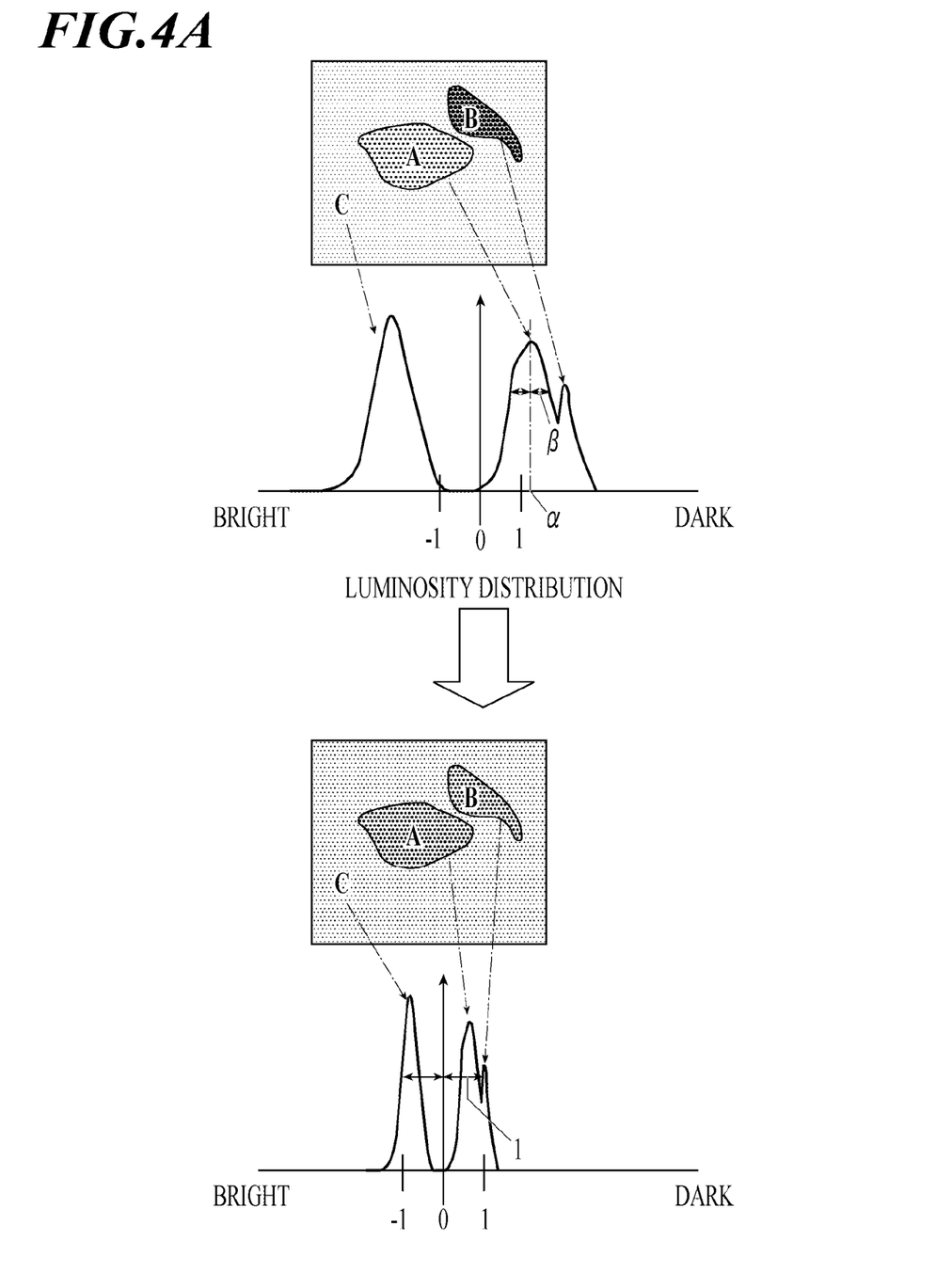
FIG. 4A shows diagrams for explaining effects of typical normalization processing.

FIG. 4A shows a case of performing normalization processing based on only the luminosity average and the luminosity variance of a whole cell image. As shown in FIG. 4A, the normalization does not take into account the proportion of stained regions A, B in the image and density difference between the stained regions A, B. When the proportion of the stained regions A, B in the image is small with respect to the back region C, the color-material density of the back region C strongly affects the normalization. Accordingly, features, such as difference in shades between the stained regions A, B with respect to standard staining condition, may not be easily recognized.

Figure 4B:
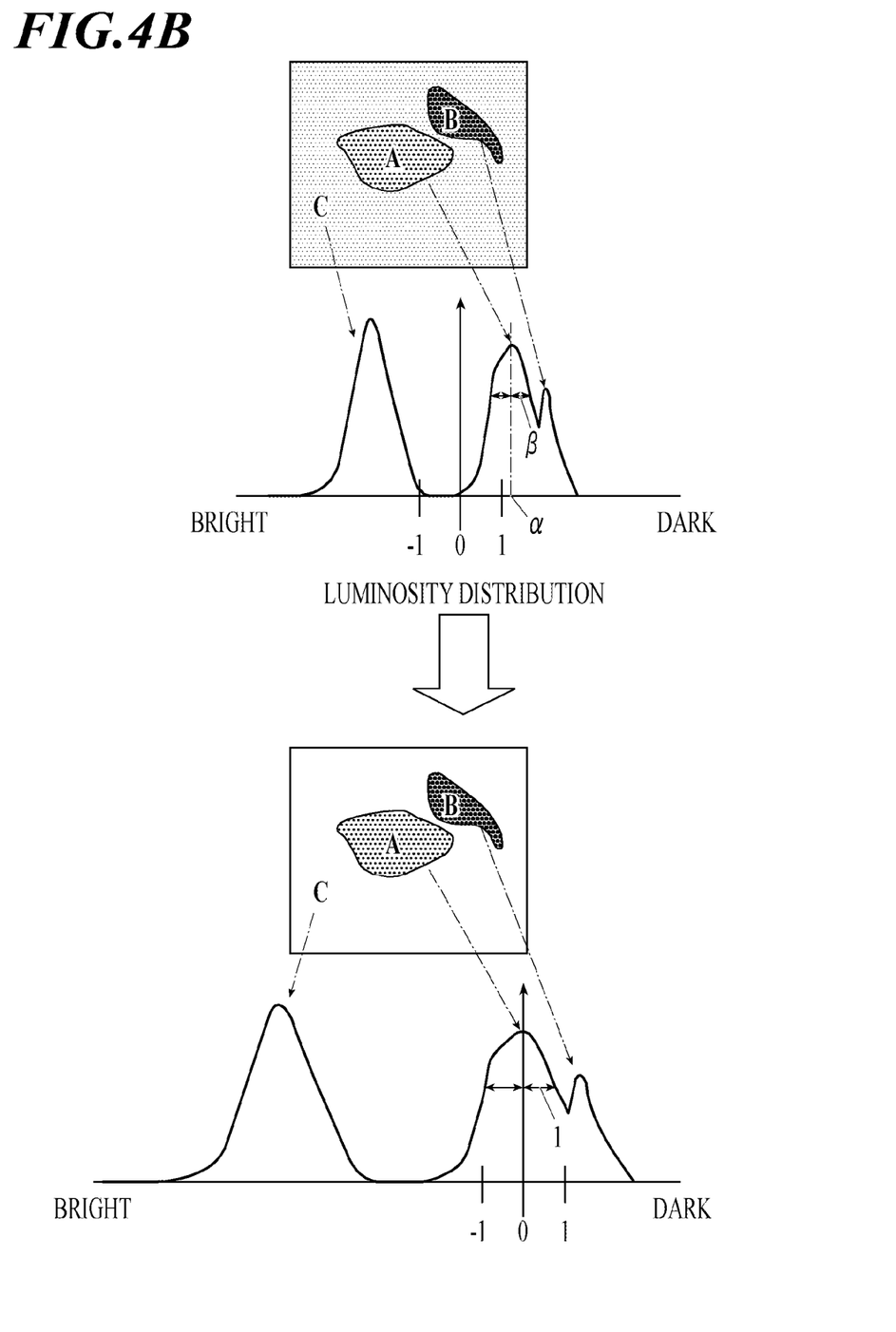
FIG. 4B shows diagrams for explaining effects of normalization processing based on a standard staining density.

FIG. 4B shows a case where the normalization processing is performed using the formula (1). As shown in FIG. 4B, the normalization is based on the stained region A, which is stained with the standard staining density, whereas effects of the color material density of the back region C are reduced. This makes it possible to utilize features, such as difference in shades between the stained region A and the stained region B, which has high staining density.

Next, normalization processing based on staining densities by regions is described.

A tissue section includes various regions, such as a tumor region, an interstitial region, and a vitreous region. These regions have different stainabilities with the same staining reagent. Assume that a cell image is normalized based on its luminosity average and luminosity valiance as a whole as described above. If an image includes an interstitial region alone, whereas another image includes an interstitial region and a tumor region, the interstitial regions of these images are normalized on the basis of different standards. As a result, comparing the interstitial regions in these two cell images does not yield a correct analysis result.

In this embodiment, for a region having a standard staining density, the luminosity average is $\alpha_2$, and the luminosity variance is $\beta_2$. The following formula is applied to a signal $X_2$ of the original image.

$$Z_2=(X_2-\alpha_2)/\sqrt{\beta_2} \qquad (2)$$

Thus, normalization processing based on the standard staining density of the region can be performed. Normalizing the respective regions with the formula (2) generates images appropriate for extracting features of the respective regions.

Next, normalization processing based on staining densities of respective types of cells is described with reference to FIG. 5. Different types of cells have different stainabilities under the same staining condition. For an extraction target cell that has the standard staining density stained under a specific staining condition and under conditions of a region to which the cell belongs, the luminosity average is $\alpha_3$ and luminosity variance is $\beta_3$. The following formula is applied to a signal $X_3$ of the original image.

$$Z_3=(X_3-\alpha_3)/\sqrt{\beta_3} \qquad (3)$$

Thus, normalization processing based on the standard staining density of the extraction target cell can be performed.

Figure 5A:
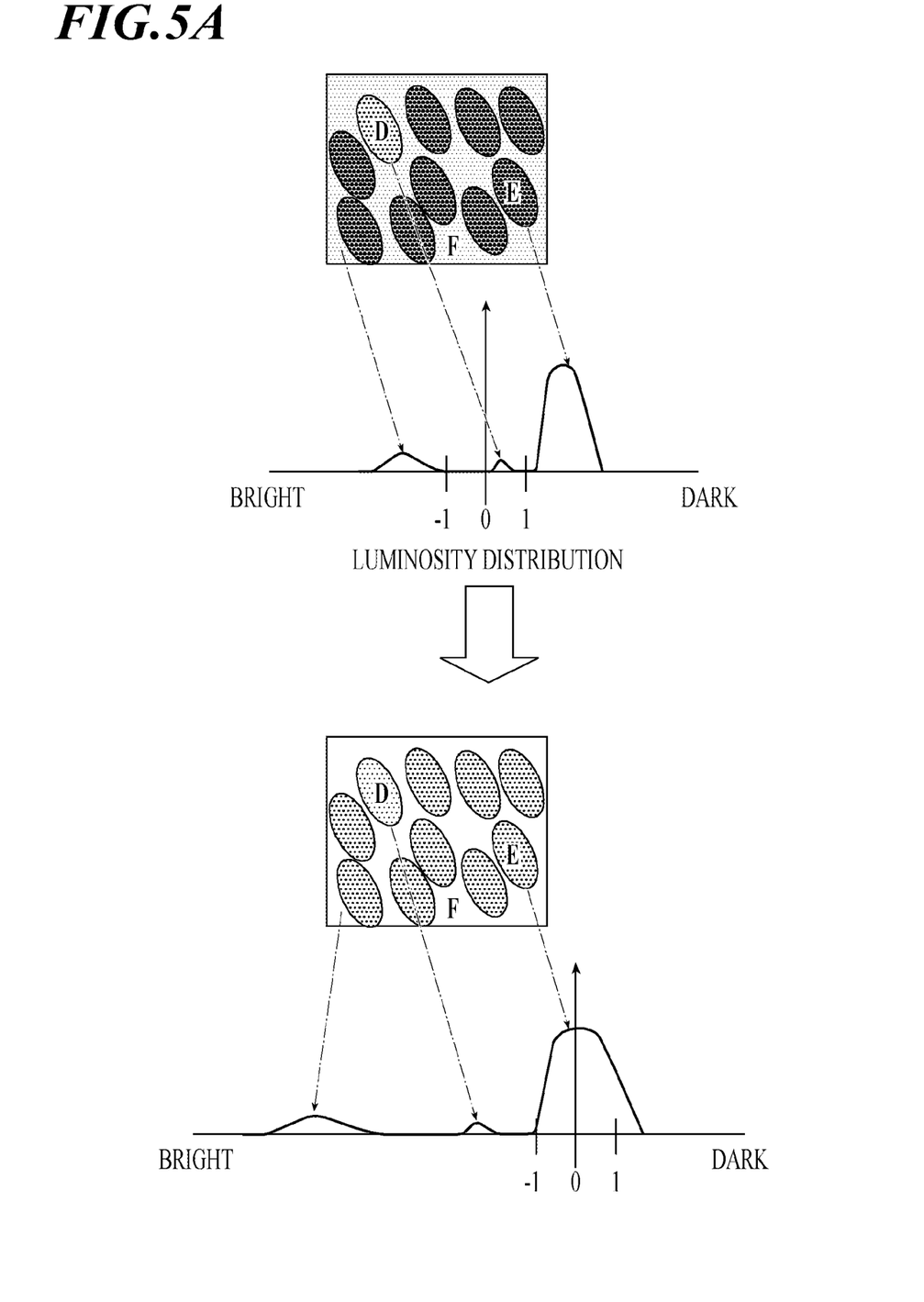
FIG. 5A shows diagrams for explaining effects of typical normalization processing.

FIG. 5A shows a case where normalization processing is performed on the basis of only the luminosity average and the luminosity variance of one image. As shown in FIG. 5A, the normalization does not take into account density distribution of extraction target cells and the number of extraction target cells in the image. The image includes, as extraction target cells, a small number of cells D having the standard staining density and a large number of cells E having a high staining density. When the image is simply normalized, difference in shades between the cells D having the standard staining density and the cells E having the high staining density is inconspicuous. This is because the normalization is based on the cells E having the high staining density.

Figure 5B:
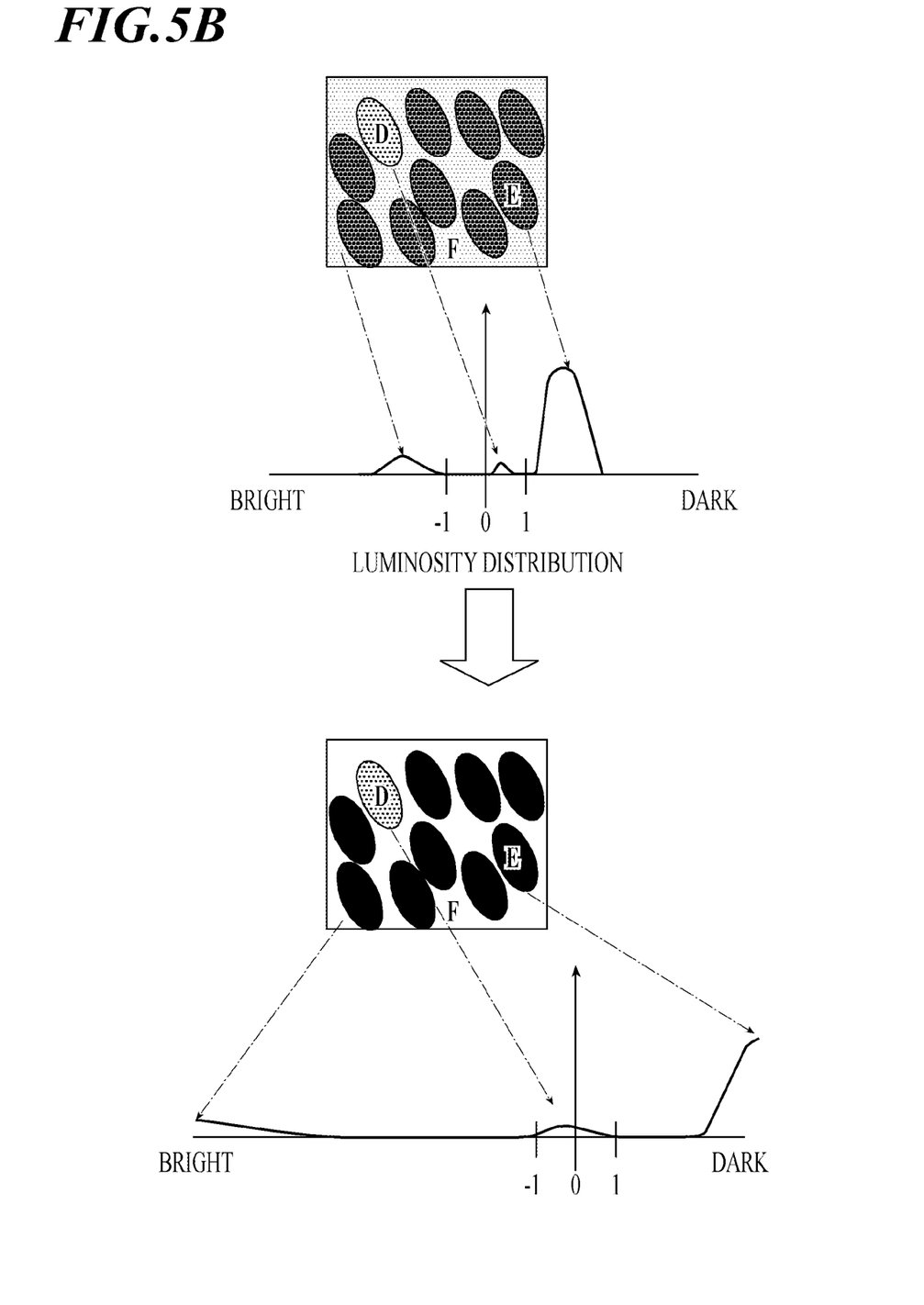
FIG. 5B shows diagrams for explaining effects of normalization processing based on characteristics of each type of cell in density changes.

FIG. 5B shows a case where normalization processing is performed using the formula (3). As shown in FIG. 5B, the image maintains information on difference in shades among cells and conspicuously shows difference in staining densities among the extraction target cells. This is because the normalization is based on the cells D having the standard staining density while reducing effects of the back region F and the cells E, which have the high staining density.

When multiple staining reagents are used for staining, it is effective to perform the normalization processing based on standard staining densities of the respective staining reagents. This generates images appropriate for extracting features on the basis of the respective staining reagents.

Further, normalization processing may be based on standard luminosity according to imaging conditions, such as imaging equipment and imaging processes. This can reduce variations in luminosity owing to different imaging conditions to extract features.

As described above, normalization processing is performed on one cell image under multiple conditions to obtain multiple processed images. Information required for the above-described normalization processing, such as luminosity averages $\alpha_1$ to $\alpha_3$ and luminosity variances $\beta_1$ to $\beta_3$ in the above examples, is input to the image processing apparatus 2A by a user beforehand and stored in the storage 25 as auxiliary information.

From multiple processed images obtained, feature quantities are extracted. On the basis of the extracted feature quantities, discrimination conditions are constructed for performing cell discrimination. Cell discrimination is then performed.

Figure 6:
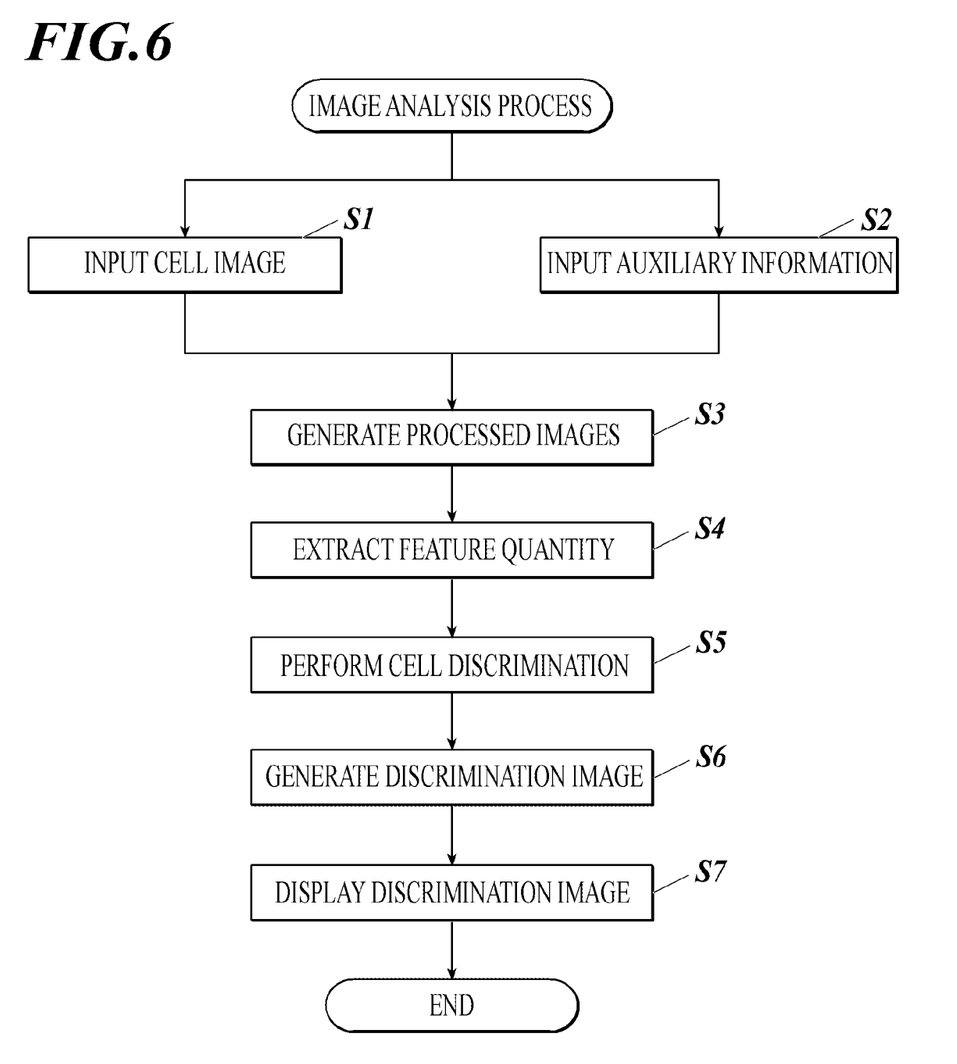
FIG. 6 is a flowchart showing an image analysis process according to the present invention.

FIG. 6 shows a flowchart of image processing by the image processing apparatus 2A. The image processing shown in FIG. 6 is performed by the controller 21 in coordination with the image analysis process program stored in the storage 25. The controller 21 performs the following process in accordance with the image analysis process program.

First, the communication I/F 24 as the image inputter inputs a cell image from the microscope-image obtaining apparatus 1A (STEP S1: image inputting).

On the other hand, a user inputs auxiliary information with the operation unit 22 as an auxiliary information inputter (Step S2: auxiliary information inputting). Herein, the auxiliary information is information relating to the cell image input in Step S1. Examples of the auxiliary information include: averages and variances of colors of respective staining reagents in staining (e.g., above-described luminosity average $\alpha_1$ and luminosity variance $\beta_1$); information on regions in the cell image, such as interstitial regions and tumor regions, and characteristics in density variations of the respective regions in staining (e.g., above-described luminosity average $\alpha_2$ and luminosity variance $\beta_3$); and characteristics in density variations of respective extraction target cells in staining (e.g., above-described luminosity average $\alpha_3$ and luminosity variance $\beta_3$).

When the cell image and the auxiliary information are input, the controller 21 as the image processor generates multiple processed images on the basis of the cell image input in Step S1 and the auxiliary information input in Step S2 (Step S3: image processing). More specifically, when multiple pieces of auxiliary information are given, such as standard staining densities, characteristics in density variations of respective regions, and characteristics in density variations of respective extraction target cells, the controller 21 performs (i) normalization processing based on standard staining densities, (ii) normalization processing as many times as the number of input regions, and (iii) normalization processing as many times as the number of types of extraction target cells. As a result, the controller 21 generates multiple processed images.

After the process in Step S3, the controller 21 as the feature quantity extractor extracts feature quantities from the multiple processed images generated in Step S3 (Step S4: feature quantity extracting). In general, examples of the feature quantities may include information on averages, standard deviation, variances, and edges of pixel values, and information on gradients in luminosity. Co-occurrence and difference among the images may be also used as feature quantities in this embodiment, as multiple processed images are input. In Step S4, the controller 21 extracts multiple feature quantities as exemplified. Conditions for extracting these feature quantities are constructed by the user beforehand and stored in the storage 25.

After the process in Step S4, the controller 21 as the discriminator performs cell discrimination (Step S5: discriminating). More specifically, the controller 21 constructs discrimination conditions for appropriately discriminating types of cells on the basis of the feature quantities extracted in Step S4. To construct the discrimination conditions machine learning, such as support vector machines and random forests, are generally used.

When a support vector machine is used to perform cell discrimination, the following process is executed, for example. The storage 25 stores a correct discrimination image(s) beforehand. The correct discrimination image gives feature quantities of samples (cells) in the image and correct class labels (types of cells) for the respective samples. In Step S5, the controller 21 learns, from a set of samples the classes of which are known, stochastic correspondence relationships between feature quantities and the classes as knowledge, and obtains parameters (discrimination conditions) for performing linear classification of data. Next, according to the discrimination conditions, the controller 21 determines classes to which the respective feature quantities extracted in Step S4 belong. Thus, the controller 21 discriminates types of individual cells in the cell image.

After Step S5, the controller 21 generates a discrimination image (Step S6).

Figure 7A:
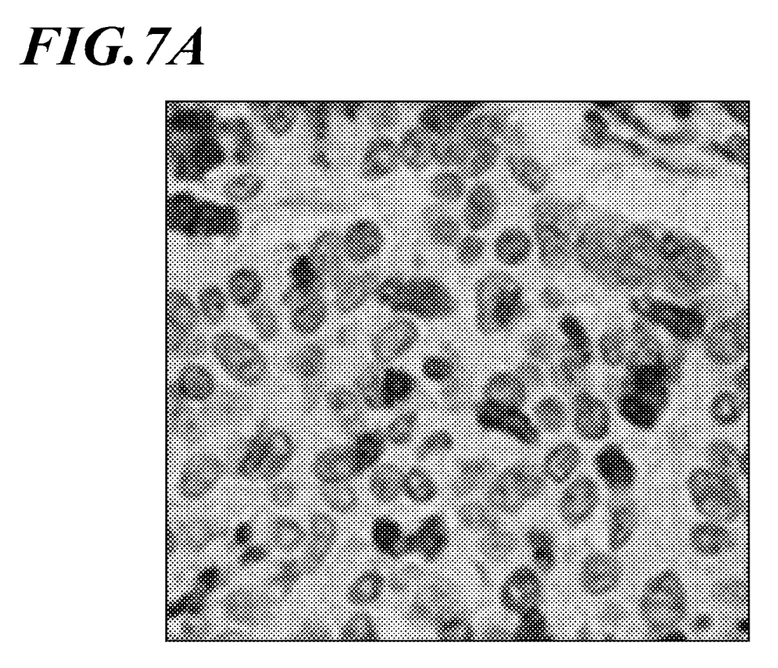
FIG. 7A is an example of a cell image.
Figure 7B:
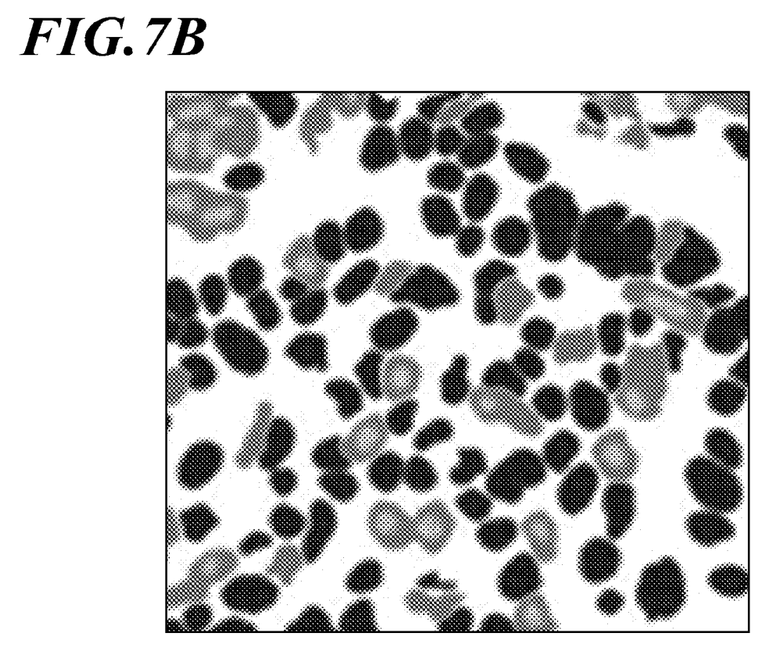
FIG. 7B is an example of a discrimination image generated on the basis of the cell image shown in FIG. 7A.

FIG. 7 exemplifies the discrimination image. FIG. 7A is a cell image in which (i) the tissue section is stained with the H-staining and (ii) immune cells are stained with the DAB staining. Cell discrimination is performed for this cell image. FIG. 7B shows a discrimination image in which (i) the cells are colored by types and (ii) regions stained with the DAB staining are also colored. The storage 25 stores parameters for processing beforehand, such as color conversion, conversion to monochrome image, and gradation conversion, according to information on types of cells and staining information. Using the parameters, the controller 21 performs processing on discriminated specific cells and regions to generate the discrimination image.

Next, the controller 21 causes the display 23 to display the discrimination image generated in Step S6 (Step S7). Along with the discrimination image, the display 23 may also display information including the shape, the size, and the number of cells for the respective types into which the cells are classified. This allows the user to visually recognize the types, the number, and the shape of cells in the cell image.

As described above, the pathological diagnosis support system 10 according to the embodiment performs the image analysis process. The image analysis process includes: image inputting that is inputting a cell image; auxiliary information inputting that is inputting auxiliary information on a color of the cell image; image processing that is generating multiple processed images by performing a different image-processing process on the cell image based on the auxiliary information; feature quantity extracting that is extracting a feature quantity of a discrimination target from each of the multiple processed images; and discriminating that is discriminating the discrimination target in the cell image based on the feature quantity.

Assume that feature quantities are extracted from only one processed image as in the conventional way, for example, a cell image is normalized on the basis of the entire region thereof. In such a case, the normalization is based on the back region that covers a large part of the image. This may cause problems. For example, features of regions including a small number of cells are lost. In contrast, the above-described image analysis process generates multiple processed images on the basis of the auxiliary information. Thus, features of the respective processed images can be extracted properly to discriminate cells accurately.

More specifically, the auxiliary information is information on colors of respective specific regions in the cell image, for example. In the image processing, the image processing is performed on the respective regions to obtain multiple processed images. Herein, to perform normalization processing based on the standard staining density of each of the regions, the luminosity average and the luminosity variance of the region are used. The normalization processing takes into account stainabilities of the respective regions and generates processed images appropriate for extracting feature quantities. This can improve accuracy of cell discrimination.

Further, the auxiliary information is information on colors of respective types of extraction target cells. In the image processing, the image is processed on the basis of types of cells to obtain multiple processed images. Herein, to perform normalization processing based on the standard staining density of each type of extraction target cell, the luminosity average and the luminosity variance of the extraction target cell are used. The normalization processing takes into account stainabilities of the respective types of cells and generates processed images appropriate for extracting feature quantities. This can improve accuracy of cell discrimination.

Further, the auxiliary information is information on colors under staining conditions. In the image processing, an image is processed on the basis of staining conditions to obtain multiple processed images. Herein, to perform normalization processing based on the standard staining density of a staining reagent, the luminosity average and the luminosity variance of the staining reagent in standard staining are used. This makes it easier to obtain features regarding shades of the cell image as compared with shades under normal staining conditions. The normalization processing may be performed based on the respective staining conditions to obtain processed images for the respective staining conditions, appropriate for extracting features.

In the above embodiment, feature quantity extracting and discriminating are performed as different processes, wherein in discriminating, the support vector machine is used as an example of machine learning. However, the feature quantity extracting and the discriminating may be performed together in one network by using deep learning, which utilizes a neural network, for example. The user does not have to construct beforehand extraction conditions for extracting feature quantities and discrimination conditions. Deep learning can automatically construct the extraction conditions and discrimination conditions, on the basis of which feature extraction and cell discrimination are performed. This can omit works done by the user and streamline the image analysis process.

Other Embodiments

The above embodiment and description thereof are a preferred example of the present invention and is not intended to limit the present invention.

Although the normalization processing is performed as the image processing, this does not limit the present invention. For example, when information on colors and rough shape of extraction target cells is more important than information on texture of the cells, features relating to the texture information may be reduced before extracting features.

Further, although cells are discriminated as the discrimination target in the above embodiment, this does not limit the present invention. Regions, such as tumor regions and interstitial regions, may be discriminated.

Further, in the above description, an HDD and a nonvolatile semiconductor memory are used as examples of a computer-readable medium storing the program of the present invention. The present invention is not limited thereto, though. As other computer-readable media, a portable storage medium, such as a CD-ROM, may be used. Also, a carrier wave can be used as a medium that provides data of the program of the present invention via a communication line.

Further, the image processing apparatus may not consist of a single apparatus. The image processing apparatus may consist of multiple devices specialized for the respective components, which include the image inputter, the auxiliary information inputter, the feature quantity extractor, and the discriminator.

The detailed configuration and detailed operation of each component included in the pathological diagnosis support system 10 may also be appropriately modified without departing from the scope of the present invention.

INDUSTRIAL APPLICABILITY

The present invention is applicable to an image processing method, an image processing apparatus, and a program.

REFERENCE SIGNS LIST

1A Microscope-image obtaining apparatus
2A Image processing apparatus
21 Controller (image processor, feature quantity extractor, discriminator)
22 Operation unit (auxiliary information inputter)
23 Display
24 Communication I/F (Image inputter)
25 Storage
26 Bus
3A Cable
10 Pathological diagnosis support system

The invention claimed is:

1. An image processing method, comprising:
   image inputting comprising inputting a cell image;
   auxiliary information inputting comprising inputting auxiliary information on a color of the cell image, wherein the auxiliary information comprises information on a color of each of a type of cell;
   image processing comprising generating multiple processed images by performing a different image-processing process on the cell image based on the auxiliary information for each of the type of cell;
   feature quantity extracting comprising extracting a feature quantity of a discrimination target from each of the multiple processed images; and
   discriminating comprising discriminating the discrimination target in the cell image based on the feature quantity.

2. The image processing method according to claim 1, wherein
   the auxiliary information comprises information on a color of each of a specific region in the cell image, and
   the image processing comprises generating the multiple processed images by performing the image-processing process for each of the specific region.

3. The image processing method according to claim 2, wherein
   the image processing comprises generating the multiple processed images by performing, as the image-processing process, a normalization process that uses a luminosity average and a luminosity variance of each of the region to which a cell belongs.

4. The image processing method according to claim 1, wherein the image processing is generating the multiple processed images by performing, as the image-processing process, a normalization process that uses a luminosity average and a luminosity variance of each of the type of cell.

5. The image processing method according to claim 1, wherein
   the auxiliary information comprises information on a color of the cell image under each of a staining condition, and
   the image processing comprises generating the multiple processed images by performing the image-processing process based on the staining condition of the cell image.

6. The image processing method according to claim 5, wherein the image processing comprises generating the multiple processed images by performing, as the image-processing process, a normalization process that uses a luminosity average and a luminosity variance of each of the staining condition.

7. The image processing method according to claim 1, wherein the feature quantity extracting and the discriminating are performed together.

8. An image processing apparatus, comprising:
an image inputter that inputs a cell image;
an auxiliary information inputter that inputs auxiliary information on a color of the cell image, wherein the auxiliary information comprises information on a color of each of a type of cell; and
a hardware processor that generates multiple processed images by performing a different image-processing process on the cell image based on the auxiliary information for each of the type of cell,
extracts a feature quantity of a discrimination target from each of the multiple processed images, and
discriminates the discrimination target in the cell image based on the feature quantity.

9. A non-transitory computer-readable storage medium storing a program that causes a computer of an image processing apparatus to perform:
inputting a cell image;
inputting auxiliary information on a color of the cell image, wherein the auxiliary information comprises information on a color of each of a type of cell;
generating multiple processed images by performing a different image-processing process on the cell image based on the auxiliary information for each of the type of cell;
extracting a feature quantity of a discrimination target from each of the multiple processed images; and
discriminating the discrimination target in the cell image based on the feature quantity.

* * * * *